United States Patent

Cyrus et al.

[11] 3,996,360
[45] Dec. 7, 1976

[54] PIPERAZINE COMPOUNDS

[75] Inventors: Richard Cyrus, Ludwigshafen (Rhine); Manfred Raschack, Weisenheim am Sand, both of Germany

[73] Assignee: Knoll A.G. Chemische Fabriken, Ludwigshafen, Germany

[22] Filed: July 31, 1975

[21] Appl. No.: 600,870

[30] Foreign Application Priority Data

Aug. 12, 1974 Germany .......................... 2438725

[52] U.S. Cl. ........................... 424/250; 260/268 C; 260/268 BZ
[51] Int. Cl.² ...................................... C07D 241/04
[58] Field of Search .............. 424/250; 260/268 BZ

[56] References Cited
UNITED STATES PATENTS 2,997,473  8/1961  de Jongh et al. ............. 260/268 BZ Primary Examiner—Donald G. Daus
Assistant Examiner—Jose Tovar
Attorney, Agent, or Firm—Donald R. Bentz

[57] ABSTRACT

Cardioactive 3-methyl-3-(3,4-dialkoxybenzyl)-piperazine compounds of the formula

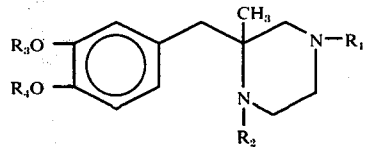

and their salts with physiologically tolerable acids; methods for making the same; pharmaceutical compositions containing the compounds as an active ingredient; and methods of treating cardiac diseases such as arrhythmia with said compounds.

43 Claims, No Drawings

PIPERAZINE COMPOUNDS

The present invention relates to piperazine compounds, to methods for their preparation, to pharmaceutical compositions containing these compounds, and to methods of treatment employing these compounds.

The anti-arrhythmic agents presently used in practice exhibit undesirable side effects such as a negative influence on the contractile force of the heart. The use of these preparations is, thus, not without problems [cf. for example, Muertz et al., Med. Mschr. 24, 239 – 245 (1970) and Bleifeld et al., Dtsch. Med. Wschr. 96, 671 – 680 (1971)]. Further, the compounds are active only over a very short period so that the thus-necessitated considerable intake of the compounds, separated by short periods of time, creates additional safety risks for patients. For these reasons it is desirable to have at one's disposal materials that do not have these disadvantages.

It has now been found that certain piperazine compounds are very suitable for the treatment of cardiac diseases. More in particular, the present invention relates to piperazine compounds of the formula

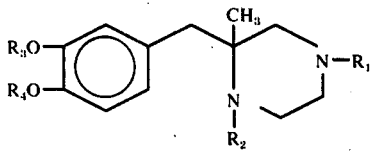

and to salts of these compounds with physiologically tolerable acids, wherein $R_1$ is hydrogen or diphenylmethyl, in the phenyl group of which the para-position may be substituted by chlorine rather than hydrogen;

$R_3$ is hydrogen, straight-chain alkyl having 1 to 5 carbon atoms, alkenyl having 3 to 4 carbon atoms, N-dialkyl aminoalkyl having 4 to 8 carbon atoms, hydroxyalkyl having 2 to 4 carbon atoms, benzoyl, benzoyl substituted by alkoxy having 1 to 4 carbon atoms in the alkoxy, pyridine carbalkoxy having 2 to 4 carbon atoms in the alkoxy, carbalkoxy having 2 to 4 carbon atoms, acyl having 1 to 4 carbon atoms, or carbethoxy methylene; and $R_3$ and $R_4$, which are the same or different, are alkyl having 1 to 4 carbon atoms.

The invention further relates to the preparation of such piperazine compounds and their salts by reduction of a piperazinone compound of the formula

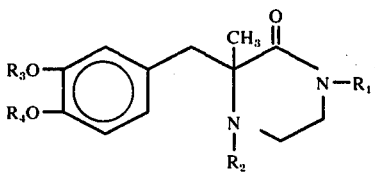

wherein $R_1 - R_4$ have their earlier meanings, with an organometallic compound. In case $R_1$ and/or $R_2$ are hydrogen in such a product, the nitrogen atoms may be subsequently substituted, and/or any free hydroxy groups can be esterified. In case $R_3$ and $R_4$ are alkyl in such a product, they may subsequently be exchanged for hydrogen or other alkyl groups. The free bases may be salified with a physiologically tolerable acid to form the aforementioned salts.

The invention further relates to therapeutic compositions containing the pyridine compounds or their salts with physiologically tolerable acids. Suitable physiologically tolerable acids include hydrochloric acid, sulfuric acid, phosphoric acid, acetic acid, malonic acid, succinic acid, citric acid, tartaric acid, lactic acid, and diamidosulfonic acid, for example.

The reduction of the piperazinone compounds to the corresponding piperazines can be accomplished with complex hydrides such as lithium aluminum hydride or dibutyl aluminum hydride in ethers, preferably diethyl or diisopropyl ether or cyclic ethers such as tetrahydrofuran or dioxane. It is recommended to work at elevated temperatures, preferably at the boiling points of the solvents employed.

Alkylation of the piperazine ring system with substituted or unsubstituted diphenylmethyl halides takes place specifically at the nitrogen atom in the 1-position. As halides, the bromide and chloride are preferred. Aromatic hydrocarbons such as benzene, toluene, and xylene, or low-boiling ketones such as acetone, methyl ethyl ketone, and diisobutyl ketone are used as solvents. Also, for example, dimethyl formamide and hexamethyl phosphoric acid triamide are suitable. The temperatures are preferably between 25° C. and 130° C. The addition of basic condensation agents such as tertiary organic bases or alkali carbonates such as potassium or sodium carbonate is recommended.

Alkylation of the nitrogen atom in the 4-position can take place in an analogous manner. When using alkyl chlorides or alkyl bromides, however, the addition of sodium iodide or potassium iodide and the use of a slight superatmospheric pressure of about 1.5 to 10 atmospheres gauge are recommended.

It is further possible to acylate the piperazine ring at the nitrogen atom in the 4-position with acyl halides, anhydrides, or esters and to reduce the acylation products to the corresponding alkyl derivatives in aliphatic or cyclic ethers such as diethyl ether, dioxane, or tetrahydrofuran, using complex hydrides.

A methyl group can also be introduced on the nitrogen atom in the 4-position by reacting piperazine with chloroformic acid ethyl ester at low temperatures in a suitable solvent, for example aromatic hydrocarbons or halo-hydrocarbons, in the presence of a base, preferably triethylamine. The acylation product obtained in this manner can be reduced very readily with comlpex hydrides.

Further, the piperazine compounds can be hydroxyalkylated at the nitrogen atom in the 4-position with alkylene oxides. As solvents, mixtures of low-boiling alcohols and aromatic hydrocarbons, preferably methanol and benzene in a ratio of 2:1, are employed. The reaction is suitably carried out at 25° – 80° C. and at a pressure of 3 – 5 atmospheres.

In these reactions at the nitrogen atom in the 4-position, the nitrogen atom in the 1-position must either be earlier substituted by the group $R_1$ or must be protected by a protective group which is later cleaved. Otherwise, the latter nitrogen atom will undergo the same reaction as the nitrogen atom in the 4-position.

The esterification of hydroxyalkyl groups takes place with the formation of alkali salts in an aprotic solvent such as dimethyl formamide or hexamethyl phosphoric acid amide using metal hydrides or metal amides such as sodium hydride or sodium amide at temperatures of 80° C. – 100° C. By the addition of a suitable acid chloride, the corresponding hydroxyalkyl ester is obtained.

The compounds of the invention are resorbed well and can therefore be administered as an oral prophylactic. They have a much less strong negative inotropic effect than certain known anti-arrhythmic agents. Further, the compounds, in anti-arrhythmic doses, cause practically no decrease in the blood pressure. Finally, the compounds antagonize the effects of biogenic amines having a vasoconstrictor action.

Those compounds in which $R_1$ is diphenylmethyl and $R_2$ is hydrogen, alkyl, or hydroxyalkyl, have shown themselves to be particularly effective. Among these, 1-diphenylmethyl-3-methyl-3-(3,4-dimethoxybenzyl)-piperazine is outstanding.

Evidence of the anti-arrhythmic effect of the new compounds is obtained in experimental animals by determination of the functional refractory period of the left auricle of the guinea pig with the aid of paired electrical stimulation employing the method of W. C. Govier, J. Pharmacol, Exp. Therap. 148, 100 – 105 (1965). In this experimental arrangement, those anti-arrhythmic agents already known for use in therapy, of differing structure and of different points of attack in the human, all distinguish themselves by lengthening the functional refractory period. The method additionally permits a determination of the effects of the substances on the contractile force of the heart muscle [cf. Reuter and Heeg, Naunyn-Schmiedeberg's Arch. Pharmak. 268, 323 – 333 (1971) and Zettler and Strubelt, Naunyn-Schmiedeberg's Arch. Pharmak. 271, 335 – 345 (1971)].

The testing of the substances in each case involves up to thirty individual experiments. For the dosage effect relationships, linear regression functions were calculated [A. Lindner, Statistische Methoden, 3rd Edition, Birkhaeuser Verlag, Basel (1969)], wherein the maximum percentage deviations from the starting value over a period of up to 60 minutes after addition of the test substance to the bath fluid were employed.

In following Table 1, column I, the optical isomers of one of the compounds of the invention and known anti-arrhythmic agents are named. Column II reports their anti-arrhythmic effect. Column III gives the inotropic effect, and column IV represents the therapeutic breadth of the compounds. The $ED_{25}$ is the effective dose which lengthens the refractory period by 25 percent or reduces the contractile force by 25 percent.

Table 1

| I<br>Antiarrhythmic Agent | II<br>Antiarrhythmic Effect<br>(Lengthening of the Refractory Period) | III<br>Inotropic Effect<br>(Decrease in Contractile Force) | IV<br>Therapeutic Breadth<br>(III/II) |
|---|---|---|---|
| N-n-propylajmaline | $ED_{25} = 0.0037$ | $ED_{25} = 0.0015$ | 0.4 |
| Antazoline | $ED_{25} = 0.164$ | $ED_{25} = 0.094$ | 0.6 |
| (D)-1-diphenylmethyl-3-methyl-3-(3,4-dimethoxybenzyl)-4-methyl-piperazine | $ED_{25} = 0.0063$ | $ED_{25} = 0.0093$ | 1.5 |
| (L)-1-diphenylmethyl-3-methyl-3-(3,4-dimethoxybenzyl)-4-methyl-piperazine | $ED_{25} = 0.0056$ | $ED_{25} = 0.0052$ | 0.9 |

It is evident from the foregoing Table that the substances of the present invention are superior, from the point of view of their efficacy, to the known materials. Further, the materials possess a greater safety margin between the desired rhythm-regularizing effect and the undesirable influence on the contractility of the heart (column IV).

Following Table 2 shows the anti-arrhythmic effect of the new substances in comparison to the known agent, ajmaline. The dose in each case is $10^{-5}$ millimoles/liter.

TABLE 2

| Antiarrhythmic Agent | Antiarrhythmic Effect (Lengthening of the refractory period in percent) |
|---|---|
| (D)-1-diphenylmethyl-3-methyl-3-(3,4-dimethoxybenzyl)-4-methyl-piperazine | 50 |
| 1-diphenylmethyl-3-methyl-3-(3,4-dimethoxybenzyl)-piperazine | 46 |
| 1-diphenylmethyl-3-methyl-3-(3,4-dimethoxybenzyl)-4-hydroxyethyl-piperazine | 55 |
| 1-(p-chlorophenyl-phenylmethyl)-3-methyl-3-(3,4-dimethoxybenzyl)-piperazine | 28 |
| (D)-1-diphenylmethyl-3-methyl-3-(3,4-dimethoxybenzyl)-piperazine | 31 |
| (D)-1-diphenylmethyl-3-methyl-3-(3,4-dimethoxybenzyl)-4-hydroxyethyl-piperazine | 72 |
| (L)-1-diphenylmethyl-3-methyl-3-(3,4-dimethoxybenzyl)-4-ethyl-piperazine | 48 |
| 1-(p-chlorophenyl-phenylmethyl)-3-methyl-3-(3,4-dimethoxybenzyl)-4-hydroxyethyl-piperazine | 55 |
| (D)-1-diphenylmethyl-3-methyl-3-(3,4-dimethoxybenzyl)-4-ethyl-piperazine | 50 |
| (D)-1-diphenylmethyl-3-methyl-3-(3,4-dimethoxybenzyl)-4-n-propyl-piperazine | 51 |
| (D)-1-diphenylmethyl-3-methyl-3-(3,4-dimethoxybenzyl)-4-n-butyl-piperazine | 31 |

TABLE 2-continued

| Antiarrhythmic Agent | Antiarrhythmic Effect (Lengthening of the refractory period in percent) |
|---|---|
| (L)-1-diphenylmethyl-3-methyl-3-(3,4-dimethoxybenzyl)-4-methyl-piperazine | 73 |
| 1-diphenylmethyl-3-methyl-3-(3,4-dimethoxybenzyl)-4-methyl-piperazine | 64 |
| Ajmaline (Comparison) | 14 |

The anti-arrhythmic effect of the new compounds can also be determined in intact test animals by experimentally-induced disturbances of the heart rhythm. If rats are continually infused intravenously with aconitine, serious disturbances of the heart-beat rhythm, such as extrasystoles, ventricular tachycardia, and ventricular flutter, which disturbances eventually lead to the death of the test animals, are evident in an electrocardiogram. By pretreatment with the substances of the invention, the appearance of these dangerous disturbances of the heart rhythm can be prevented or, on continuous administration of aconitine, can be considerably delayed. This experimental model of arrhythmia has already been tested for its probative value with clinically-tested standard therapeutic agents and is well suited for the characterization of anti-arrhythmia in experimental animals [cf. Bianchi et al., Arzneim. Forsch. 18, 845 – 850 (1968); Haas and Busch, Arzneim. Forsch. 18, 401 – 407 (1968); Haas et al., Arzneim. Forsch. 21, 1392 – 1399 (1971); Marmo, Naunyn-Schmiedeberg's Arch. Pharmak. 269, 231 – 247 (1971); Strubelt et al., Naunyn-Schmiedeberg-3 s Arch. Pharmak. 271, 346 – 360 (1971)].

Following Table 3 shows the results of the test using (D)-1-diphenylmethyl-3-methyl-3-(3,4-dimethoxybenzyl)-4-methyl-piperazine versus procainamide and sparteine. The $ED_{25}$ and $ED_{50}$ are the intravenous doses, in mg/kg, which raise the administered aconitine doses, in comparison with the aconitine control, by 25 percent or 50 percent prior to the appearance of extrasystoles, ventricular tachycardia, and ventricular flutter.

Table 3

| | | Extrasystoles | Ventricular Tachycardia | Ventricular Flutter |
|---|---|---|---|---|
| (D)-1-diphenylmethyl-3-methyl-3-(3,4-dimethoxybenzyl)-4-methyl-piperazine | $ED_{25}$ | 0.94 | 0.94 | 0.84 |
| | $ED_{50}$ | 1.21 | 1.26 1.23 | |
| Procainamide | $ED_{25}$ | 6.8 | 6.8 | + |
| | $ED_{50}$ | 52.6 | 29.1 | + |
| Sparteine | $ED_{25}$ | + | 4.4 | + |
| | $ED_{50}$ | + | 9.5 | + |

+ = no dose-dependent effect demonstrable.

Further, the compounds of the invention, in comparison with the substances heretofore used in therapy, possess an outstanding long term effect. If one treats, for example, rats perorally with 400 mg/kg of (D)-1-diphenylmethyl-3-methyl-3-(3,4-dimethoxybenzyl)-4-methyl-piperazine, a 68 percent higher dose of aconitine is required before the appearance of extrasystoles, a 75 percent higher dose of aconitine is required before the appearance of ventricular tachycardia, and a 70 percent higher dose of aconitine is required before the appearance of ventricular flutter — in comparison with untreated test animals — eight hours after administration. The corresponding values for procainamide are 16, 12, and 29 percent.

The piperazine compounds and their salts with physiologically tolerable acids may be orally or parenterally administered. The dose for intravenous or intramuscular application is about 0.5 – 5.0 mg/kg/day and is about 2 – 20 mg/kg/day for oral administration. For administration, conventional galenic preparations such as tablets, dragees, capsules, and solutions can be employed.

The starting materials for the reactions described above have not heretofore been described in the prior art. Their preparation takes place according to known techniques and several examples of the preparation are given below.

Preparation of the Starting Materials

1.

A. 126.6 g of 3,4-dimethoxybenzyl-α-alanine-methylester (cf. Dutch patent publication 650822) are dissolved in 250 ml of toluene and combined with 58.3 g of freshly-distilled benzaldehyde. The reaction solution is heated under reflux with a water separator. After one hour, the solvent is evaporated in vacuum. The crude benzal ester is dissolved in 300 ml of methanol and hydrogenated with Raney nickel. After two hours, the catalyst is filtered off and the filtrate is concentrated to dryness in vacuum. With stirring and ice cooling, the solid is combined with 167 ml of 3N-hydrochloric acid. After a short time, the hydrochloride of N-benzyl-3,4-dimethoxybenzyl-α-alanine-methylester begins to crystallize. m.p. = 185° C. The hydrochloride is combined with 170 ml of aqueous ammonium hydroxide solution and 250 ml of toluene and stirred. The organic phase is separated, washed free of halide with water, and dried over magnesium sulfate. After removal of the solvent, 154 g (90 percent of theory) of N-benzyl-(3,4-dimethoxybenzyl)-α-alanine methylester is obtained as an oil, which solidifies in a crystalline manner. m.p. = 43° – 45° C.

If an optically-active starting material is used, one obtains in the same yield: (D)-N-benzyl-3,4-dimethoxybenzyl-α-alanine-methylester m.p.$_{Base}$ = 53° – 55° C.; m.p.$_{HCl}$ = 197° – 199° C. (H$_2$O); [α]$_D^{20}$ = –82.2° (c = 1, methanol); and (L)-N-benzyl-3,4-dimethoxybenzyl-α-alanine-methylester m.p.$_{Base}$ = 54° – 55° C.; m.p.$_{HCl}$ = 197° – 199° C.; [α]$_D^{20}$ = +82.6° (c = 1, methanol).

B. 18.6 g of N-benzyl-3,4-dimethoxybenzyl-α-alanine-methylester are dissolved in 26 ml of glacial acetic acid, cooled to 5° C., and combined with 3.6 g of ice. Over a period of an hour, a solution of 4.5 g of potassium cyanide in 8.8 ml of water is added dropwise at 5° – 10° C.

After one hour, the reaction batch is stirred for 18 hours at 40° C. and then cooled to about 0° C. The precipitated crystals are filtered off, washed with 20 ml of ice water, and dried. 18.9 g (95.3 percent of theory) of N-benzyl-N-cyanomethyl-3,4-dimethoxybenzyl-α-alanine-methylester are obtained. m.p. = 94° – 96° C. (methanol).

In the same manner, the same yield is obtained of (D)-N-benzyl-N-cyanomethyl-3,4-dimethoxyphenyl-α-alanine-methylester m.p. = 108° C. (methanol); $[\alpha]_D^{20}$ = −15.1° (c = 1, methanol); and (L)-N-benzyl-N-cyanomethyl-3,4-dimethoxyphenyl-α-alanine-methylester m.p. = 109° C.; $[\alpha]_D^{20}$ = +15.2° (c = 1, methanol).

C. 38.2 g of N-benzyl-N-cyanomethyl-3,4-dimethoxybenzyl-α-alanine-methylester, 200 ml of toluene, 400 ml of methanol saturated with gaseous ammonia, and a teaspoonful of anhydrous Raney cobalt are heated to 40° C. in an autoclave. Hydrogen is introduced at a pressure of 100 atmospheres gauge. After 1 – 2 hours, the reaction is concluded. The mixture is filtered and the filtrate is concentrated. The residue is recrystallized from methanol. 32.5 g (91.7 percent of theory) of 3-methyl-3-(3,4-dimethoxybenzyl)-4-benzyl-piperazinone-(2) are obtained. m.p. = 149° C.

Analogously, the same yield is obtained of (D)-3-methyl-3-(3,4-dimethoxybenzyl)-4-benzyl-piperazinone-(2) m.p. = 183° C.; $[\alpha]_D^{20}$ = −24.1° (c = 1, methanol); and (L)-3-methyl-3-(3,4-dimethoxybenzyl)-4-benzyl-piperazinone-(2) m.p. = 183° C.; $[\alpha]_D^{20}$ = +24.1° (c = 1, methanol).

D. 13.4 g of 3-methyl-3-(3,4-dimethoxybenzyl)-4-benzyl-piperazinone-(2) are suspended in 80 ml of glacial acetic acid and hydrogenated at room temperature with palladium black and hydrogen. After 30 minutes, the mixture is freed of catalyst by filtration and the solvent is distilled off under reduced pressure. The residue is dissolved in 25 ml of chloroform and combined with 20 percent ammonium hydroxide solution until there is a strongly alkaline reaction. After separation of the organic phase, the latter is extracted with three 10 ml portions of water. The chloroform phase is evaporated to dryness under reduced pressure. This is freed of residual water by the addition of toluene and its distillative removal in vacuum. 9.9 g (99.5 percent of theory) of 3-methyl-3-(3,4-dimethoxybenzyl)-piperazinone-(2) are obtained. m.p. = 147° – 148° C. (isopropanol).

In the same yield are obtained analogously: (D)-3-methyl-3-(3,4-dimethoxybenzyl)-piperazinone-(2) m.p. = 68° – 70° C. (diethylether); $[\alpha]_D^{20}$ = +41.9° (c = 1, methanol); and (L)-3-methyl-3-(3,4-dimethoxybenzyl)-piperazinone-(2) m.p. = 68° – 70° C. (diethylether); $[\alpha]_D^{20}$ = −41.8° (c = 1, methanol).

2.

7.7 g of 3-methyl-3-(3,4-dimethoxybenzyl)-piperazinone-(2) are suspended in 77 ml of dry dimethylformamide and combined with 8.2 g of dry potassium carbonate. A solution of 4.3 g of methyl iodide in 8 ml of dimethylformamide is added dropwise with stirring. After further stirring for 12 hours, the mixture is filtered and the filtrate evaporated. The residue is dissolved in 30 ml of methylene chloride and the solution is filtered. The solution is washed with water until free of halide and the solvent is distilled off. An oil remains which is dissolved in 80 ml of diisopropyl ether at the boiling point. On cooling, 6.6 g (81.6 percent of theory) of 3-methyl-3-(3,4-dimethoxybenzyl)-4-methyl-piperazinone-(2) crystallize. m.p. = 95° C.

In an analogous fashion, the same yields are obtained of the following: (D)-3-methyl-3-(3,4-dimethoxybenzyl)-4-methyl-piperazinone-(2) m.p. = 124° – 126° C. (isopropanol); $[\alpha]_D^{20}$ = −49° (c = 1, methanol); and (L)-3-methyl-3-(3,4-dimethoxybenzyl)-4-methyl-piperazinone-(2) m.p. = 126° C. (isopropanol); $[\alpha]_D^{20}$ = +49.3° (c = 1, methanol).

3.

A. 4.8 g of 50 percent sodium hydride in mineral oil are suspended in 100 ml of dry dimethylformamide and 35.4 g of 3-(3,4-dimethoxybenzyl)-4-benzyl-3-methyl-piperazinone-(2), dissolved in 100 ml of dry dimethylformamide, are added dropwise at room temperature with stirring, whereby hydrogen is evolved. The mixture is stirred for a further ten minutes at 40° C. In the course of 20 minutes, a solution of 25 g of diphenylmethylbromide in 100 ml of dry dimethylformamide is added. After stirring for 60 hours at room temperature, the sodium bromide formed is removed by filtration. The filtrate is evaporated, taken up in benzene, and filtered. The filtrate is concentrated and the residue recrystallized from diisopropylether. 49.5 g (95 percent of theory) of 1-diphenylmethyl-3-methyl-3-(3,4-dimethoxybenzyl)-4-benzyl-piperazinone-(2) are obtained. m.p. = 158° – 159° C.

In an analogous fashion, (D)-1-diphenylmethyl-3-methyl-3-(3,4-dimethoxybenzyl)-4-benzyl-piperazinone-(2) and (L)-1-diphenyl-methyl-3-methyl-3-(3,4-dimethoxybenzyl)-4-benzyl-piperazinone-(2) are obtained in the same yield. Neither substance is isolated in pure form; rather, both materials are further worked up as crude products.

B. 36 g of 1-diphenylmethyl-3-methyl-3-(3,4-dimethoxybenzyl)-4-benzyl-piperazinone-(2) are dissolved in 200 ml of glacial acetic acid and combined with 2 g of 10 percent palladium black. Hydrogen is introduced under pressure at room temperature. After one hour, the catalyst is filtered off, the filtrate is evaporated, and the residue is dispersed between 100 ml of chloroform and 20 ml of concentrated ammonium hydroxide solution. After separation of the organic phase, the phase is extracted with two 20 ml portions of water and evaporated to dryness. The crystalline residue is recrystallized from isopropyl alcohol. 19.35 g (90 percent of theory) of 1-diphenylmethyl-3-methyl-3-(3,4-dimethoxybenzyl)-piperazinone-(2) are obtained. m.p. = 143° C.

In a corresponding manner are obtained, in the same yield: (D)-1-diphenylmethyl-3-methyl-3-(3,4-dimethoxybenzyl)-piperazinone-(2) m.p. = 166° C. (isopropanol); $[\alpha]_D^{20}$ = +16.5° (c = 1, methanol); and (L)-1-diphenylmethyl-3-methyl-3-(3,4-dimethoxybenzyl)-piperazinone-(2) m.p. = 167° C. (isopropanol); $[\alpha]_D^{20}$ = −16.4° (c = 1, methanol)

C. 39.8 g of 3-methyl-3-(3,4-dimethoxybenzyl)-piperazinone-(2) in 200 ml of dry dimethylformamide are added dropwise with stirring to a suspension of 6.55 g of a sodium hydride dispersion in mineral oil and 200 ml of dry dimethylformamide. After 30 minutes, a solution of 39.5 g of diphenylmethylbromide in 100 ml of dry dimethylformamide is added rapidly dropwise to the reaction solution and the batch is stirred further for 65 hours at room temperature.

The reaction mixture is concentrated, dissolved in 200 ml of chloroform, and washed free of halide with water. After distillation of the solvent in vacuum, a honey-colored oil, which is re-crystallized from isopropanol, is obtained. 43 g (69 percent of theory) of 1-diphenylmethyl-3-methyl-3-(3,4-dimethoxybenzyl)-piperazinone-(2) are obtained. m.p. = 142° C.

In an analogous manner, and in the same yield, are obtained: (D)-1-diphenylmethyl-3-methyl-3-(3,4-dimethoxybenzyl)piperazinone-(2) m.p. = 166° C. (isopropanol; $[\alpha]_D^{20} = +16.5°$ (c = 1, methanol); and (L)-1-diphenylmethyl-3-methyl-3-(3,4-dimethoxybenzyl)-piperazinone-(2) m.p. = 167° C. (isopropanol); $[\alpha]_D^{20} = -16.3°$ (c = 1, methanol).

D. In a similar fashion, 1-(p-chlorophenyl-phenylmethyl)-3-methyl-3-(3,4-dimethoxybenzyl)-piperazinone-(2) is obtained m.p. = 95° C. (diisopropylether); as well as (D)-1-(p-chlorophenyl-phenylmethyl)-3-methyl-3-(3,4-dimethoxybenzyl)-piperazinone-(2) m.p. = 148° C. (isopropanol); $[\alpha]_D^{20} = +26°$ (c = 1, methanol); and (L)-1-(p-chlorophenyl-phenylmethyl)-3-methyl-3-(3,4-dimethoxybenzyl)-piperazinone-(2) m.p. = 147° C. (isopropanol); $[\alpha]_D^{20} = -26.2°$ (c = 1, methanol).

7.9 g of 1-diphenylmethyl-3-methyl-3-(3,4-dimethoxybenzyl)-piperazinone-(2) [cf. "Preparation", part 3(C) above] are dissolved in 100 ml of dry acetone and combined with 5.5 g of dry potassium carbonate. 2.8 g of methyl iodide in 30 ml of dry acetone are added dropwise with stirring at room temperature over a period of 2 hours. After stirring for 12 hours at room temperature, the mixture is filtered and the filtrate is evaporated. The oily residue is dissolved in 100 ml toluene, washed free of halide with water, and evaporated. An oil is obtained which is recrystallized from diisopropylether. 6.5 g (79.6 percent of theory) of 1-diphenylmethyl-3-methyl-3-(3,4-dimethoxybenzyl)-4-methyl-piperazinone-(2) are obtained. m.p. = 122° C.

In an analogous fashion are obtained: (D)-1-diphenylmethyl-3-methyl-3-(3,4-dimethoxybenzyl)-4-methyl-piperazinone-(2)-hydrochloride m.p. = 168° – 170° C. (ethanol); $[\alpha]_D^{20} = +33.3°$ (c = 1, chloroform); and (L)-1-diphenylmethyl-3-methyl-3-(3,4-dimethoxybenzyl)-4-methyl-piperazinone-(2)-hydrochloride. m.p. = 170° C. (ethanol); $[\alpha]_D^{20} = -33.2°$ (c = 1, chloroform); and (D)-1-chlorophenyl-phenylmethyl)-3-methyl-3-(3,4-dimethoxybenzyl)-4-methyl-piperazinone-(2)-hydrochloride m.p. = 180° – 182° C. (acetone-diethylether); $[\alpha]_D^{20} = +12.5°$ (c = 1, methanol); and (L)-1-(p-chlorophenyl-phenylmethyl)-3-methyl-3-(3,4-dimethoxybenzyl)-4-methyl-piperazinone-(2)-hydrochloride m.p. = 180° – 182° C. (acetone-diethylether); $[\alpha]_D^{20} = -12.3°$ (c = 1, methanol).

A better understanding of the present invention and of its many advantages will be had by referring to the following specific examples, given by way of illustration.

EXAMPLE 1

13.2 g of 3-methyl-3-(3,4-dimethoxybenzyl)-piperazinone-(2) [cf. "Preparation", part 1(D) above] are dissolved in 200 ml of absolute tetrahydrofuran and the solution is introduced dropwise with stirring over a period of one hour into a boiling suspension of 5.5 g of lithium aluminum hydride in 100 ml of absolute tetrahydrofuran. After three hours, the excess reducing agent, as well as the complex formed, are destroyed and the inorganic salts are filtered off. The filtrate is concentrated and the remaining oil is distilled in vacuum. At 188° – 190° C. (0.05 mm Hg), 11.2 g (90 percent of theory) of 3-methyl-3-(3,4-dimethoxybenzyl)-piperazine are obtained.

In an analogous fashion and in a similar yield, the following are obtained: (D)-3-methyl-3-(3,4-dimethoxybenzyl)-piperazine b.p. = 178° – 180° C. (0.05 mm Hg); $[\alpha]_D^{20} = +15.5°$ (c = 1, methanol); and (L)-3-methyl-3-(3,4-dimethoxybenzyl)-piperazine b.p. = 178° – 181° C. (0.05 mm Hg); $[\alpha]_D^{20} = -15.6°$ (c = 1, methanol).

EXAMPLE 2

25 g of 3-methyl-(3,4-dimethoxybenzyl)-piperazine (cf. Example 1) are dissolved in 150 ml acetone, combined with 27.6 g of potassium carbonate and 0.5 g of potassium iodide, and heated to boiling with stirring. 27.6 g of diphenylmethylbromide in 50 ml of acetone are added to the reaction solution. Thereafter, the mixture is heated for five hours under reflux. The inorganic salt is filtered off and the filtrate concentrated. The residue is taken up in 100 ml of toluene and washed with three 10 ml portions of water. The organic phase is evaporated to dryness in vacuum. The oily residue is dissolved in 50 ml of diethyl ether. On cooling, 35.4 g (85 percent of theory) of 1-diphenylmethyl-3-methyl-3-(3,4-dimethoxybenzyl)-piperazine crystallize out. m.p. = 123° C.

In an analogous fashion, and in similar yields, the following compounds are obtained: (D)-1-diphenylmethyl-3-methyl-3-(3,4-dimethoxybenzyl)-piperazine m.p. = 138° C. (diisopropylether; $[\alpha]_D^{20} = +19.5°$ (c = 1, methanol); and (L)-1-diphenylmethyl-3-methyl-3-(3,4-dimethoxybenzyl)-piperazine m.p. = 139° C. (diisopropylether); $[\alpha]_D^{20} = -19.1°$ (c = 1, methanol)

EXAMPLE 3

If 3-methyl-3-(3,4-dimethoxybenzyl)-piperazine is reacted with p-chlorophenyl-phenylmethyl chloride in methyl ethyl ketone according to Example 2, 1-(p-chlorophenyl-phenylmethyl)-3-methyl-3-(3,4-dimethoxybenzyl)-piperazine is obtained in 80 percent yield after a twelve-hour reaction period. The hydrochloride has a melting point of 235° – 237° C. (isopropanol).

In an analogous fashion and in the same yield, (D)-1-(p-chlorophenyl-phenylmethyl)-3-methyl-3-(3,4-dimethoxybenzvl)-piperazine is obtained as a glass-like solid hydrate. According to a Karl Fischer water analysis, the product contains 10 mols of water, $[\alpha]_D^{20} = +9°$ (c = 2.2, methanol).

In the same yield, (L)-1-(p-chlorophenyl-phenylmethyl)-3-methyl-3-(3,4-dimethoxybenzyl)-piperazine is obtained as a glasslike solidified resin without a definite melting point. $[\alpha]_D^{20} = -15.4°$ (c = 1.5, methanol).

EXAMPLE 4

6.4 g of 1-diphenylmethyl-3-methyl-3-(3,4-dimethoxybenzyl)-piperazine (cf. Example 2) are dissolved in 60 ml of acetone and combined with 4.2 g of dry potassium carbonate. Then, with good stirring a solution of 2.2 g of methyl iodide in 20 ml of acetone is added dropwise at 25° C. The reaction mixture is stirred for twelve hours at room temperature. The mixture is filtered and the filtrate condensed. The residue is stirred with 50 ml of toluene and filtered. The toluene solution is washed free of halide with water and evaporated to dryness. A honey-yellow oil remains, which is dissolved in 50 ml of diethyl ether. After the introduction of hydrogen chloride, the dihydrochloride formed is suction-filtered, washed with two 20 ml portions of diethyl ether, dried, and recrystallized from ethyl alcohol. 6.2 g (80 percent of theory) of 1-diphenylmethyl-3-methyl-3-(3,4-dimethoxybenzyl)-4-methyl-piperazine are obtained. m.p. = 193° C.

In an analogous manner and in a similar yield the following are obtained as a crystalline base: (D)-1-diphenylmethyl-3-methyl-3-(3,4-dimethoxybenzyl)-4-methyl-piperazine. m.p. = 102° C. (diisopropylether); $[\alpha]_D^{20} = -20.5°$ (c = 1, methanol); and (L)-1-diphenylmethyl-3-methyl-3-(3,4-dimethoxybenzyl)-4-methylpiperazine m.p. = 101° C. (diisopropylether); $[\alpha]_D^{20} = +20.5°$ (c = 1, methanol).

In an analogous fashion, the following compounds are obtained:

a. (D)-1-diphenylmethyl-3-methyl-3-(3,4-dimethoxybenzyl)-4-ethyl-piperazine
m.p. = 122° C. (isopropanol); $[\alpha]_D^{20} = -16°$ (c = 1, methanol)

$a_1$. (L)-1-diphenylmethyl-3-methyl-3-(3,4-dimethoxybenzyl)-4-ethyl-piperazine m.p. = 123° C. (isopropanol); $[\alpha]_D^{20} = +16.3°$ (c = 1, methanol)

b. (D)-1-diphenylmethyl-3-methyl-3-(3,4-dimethoxybenzyl)-4-n-propyl-piperazine m.p. = 100° C. (isopropanol); $[\alpha]_D^{20} = -13.5°$ (c = 1, methanol)

$b_1$. (L)-1-diphenylmethyl-3-methyl-3-(3,4-dimethoxybenzyl)-4-n-propyl-piperazine m.p. = 101° C. (isopropanol); $[\alpha]_D^{20} = +13.1°$ (c = 1, methanol)

c. (D)-1-diphenylmethyl-3-methyl-3-(3,4-dimethoxybenzyl)-4-n-butyl-piperazine m.p. = 96° (diisopropylether); $[\alpha]_D^{20} = -13.8°$ (c = 1, methanol)

$c_1$. (L)-1-diphenylmethyl-3-methyl-3-(3,4-dimethoxybenzyl)-4-n-butyl-piperazine m.p. = 95° C. (diisopropylether); $[\alpha]_D^{20} = +14°$ (c = 1, methanol)

d. (D)-1-diphenylmethyl-3-methyl-3-(3,4-dimethoxybenzyl)-4-n-hexyl-piperazine $[\alpha]_D^{20} = -1.3°$ (c = 1, chloroform); $[\alpha]_{334\ nm}^{20} = -59.9°$ (c = 1, chloroform)

$d_1$. (L)-1-diphenylmethyl-3-methyl-3-(3,4-dimethoxybenzyl)-4-n-hexyl-piperazine $[\alpha]_{334\ nm}^{20} = +60°$ (c = 1, chloroform)

e. (D)-1-diphenylmethyl-3-methyl-3-(3,4-dimethoxybenzyl)-4-n-heptyl-piperazine $[\alpha]_D^{20} = -1.9°$ (c = 1, chloroform); $[\alpha]_{334\ nm}^{20} = -65.9$ (c = 1, chloroform)

$e_1$. (L)-1-diphenylmethyl-3-methyl-3-(3,4-dimethoxybenzyl)-4-n-heptyl-piperazine $[\alpha]_D^{20} = +2.0$ (c = 1, chloroform); $[\alpha]_{334\ nm}^{20} = +66.5°$ (c = 1, chloroform)

f. (D)-1-diphenylmethyl-3-methyl-3-(3,4-dimethoxybenzyl)-4-n-octyl-piperazine $[\alpha]_D^{20} = -1.6°$ (c = 1, chloroform); $[\alpha]_{334\ nm}^{20} = -64.3°$ (c = 1, chloroform)

$f_1$. (L)-1-diphenylmethyl-3-methyl-3-(3,4-dimethoxybenzyl)-4-n-octyl-piperazine $[\alpha]_D^{20} = +1.5°$ (c = 1, chloroform); $[\alpha]_{334\ nm}^{20} = +63.8$ (c = 1, chloroform)

g. (D)-1-diphenylmethyl-3-methyl-3-(3,4-dimethoxybenzyl)-4-allyl-piperazine-dihydrochloride m.p. = 227° C. (ethanol); $[\alpha]_D^{20} = +20.5°$ (c = 1, chloroform)

$g_1$. (L)-1-diphenylmethyl-3-methyl-3-(3,4-dimethoxybenzyl)-4-allyl-piperazine-dihydrochloride m.p. = 227° C. (ethanol); $[\alpha]_D^{20} = -20.5°$ (c = 1, chloroform)

h. (D)-1-diphenylmethyl-3-methyl-3-(3,4-dimethoxybenzyl)-4-(1-yl-2-butene)-piperazine-dihydrochloride m.p. = 212° C. (ethanol); $[\alpha]_D^{20} = -18°$ (c = 1, chloroform)

$h_1$. (L)-1-diphenylmethyl-3-methyl-3-(3,4-dimethoxybenzyl)-4-(1-yl-2-butene)-piperazine-dihydrochloride m.p. = 212° C. (ethanol); $[\alpha]_D^{20} = +18°$ (c = 1, chloroform)

i. (D)-1-diphenylmethyl-3-methyl-3-(3,4-dimethoxybenzyl)-4-(N-diethylaminoethyl)-piperazine-trihydrochloride m.p. = 211° C. (isopropanol); $[\alpha]_{334\ nm}^{20} = -18.5°$ (Base) (c = 1, chloroform)

$i_1$. (L)-1-diphenylmethyl-3-methyl-3-(3,4-dimethoxybenzyl)-4-(N-diethylaminoethyl)-piperazine-trihydrochloride m.p. = 210° C. (isopropanol); $[\alpha]_{334\ nm}^{20} = +18.8°$ (Base) (c = 1, chloroform)

j. (D)-1-diphenylmethyl-3-methyl-3-(3,4-dimethoxybenzyl)-4-(N-diethylaminopropyl)-pipeazine-trihydrochloride m.p. = 190° C. (isopropanol); $[\alpha]_{334\ nm}^{20} = -16.4$ (Base) (c = 1, chloroform)

$j_1$. (L)-1-diphenylmethyl-3-methyl-3-(3,4-dimethoxybenzyl)-4-(N-diethylaminopropyl)-piperazine-trihydrochloride m.p. = 193° C. (isopropanol); $[\alpha]_{334\ nm}^{20} = +16.1$ (Base) (c = 1, chloroform)

k. (D)-1-diphenylmethyl-3-methyl-3-(3,4-dimethoxybenzyl)-4-carbethoxymethylene-piperazine-dihydrochloride.2.5 $H_2O$ m.p. = 148° - 150° C. (ethanol); $[\alpha]_{334\ nm}^{20} = +17.3°$ (c = 1, methanol) $k_1$. (L)-1-diphenylmethyl-3-methyl-3-(3,4-dimethoxybenzyl)-4-carbethoxymethylene-piperazine-dihydrochloride.2.5 $H_2O$ m.p. = 150°C. (ethanol); $[\alpha]_{334\ nm}^{20} = -17.5°$ (c = 1, methanol)

l. 1-(p-chlorophenyl-phenylmethyl)-3-methyl-3-(3,4-dimethoxybenzyl)-4-methyl-piperazine-dihydrochloride.$H_2O$ m.p. = 175° - 177° C. (isopropanol)

$l_1$. (D)-1-(p-chlorophenyl-phenylmethyl)-3-methyl-3-(3,4-dimethoxybenzyl)-4-methyl-piperazine-dihydrochloride m.p. = 204° C. (isopropanol); $[\alpha]_{334\ nm}^{20} = -9.3°$ (c = 1, methanol); and $l_2$. (L)-1-(p-chlorophenyl-phenylmethyl)-3-methyl-3-(3,4-dimethoxybenzyl)-4-methyl-piperazine-dihydrochloride m.p. = 204° C. (isopropanol); $[\alpha]_{334\ nm}^{20} = +9.8$ (c = 1, methanol).

EXAMPLE 5

21.6 g of 1-diphenylmethyl-3-methyl-3-(3,4-dimethoxybenzyl)-piperazine (cf. Example 2) are dissolved with 5.2 g of triethylamine in 200 ml of dry toluene. Then a solution of 5.4 g of chloroformic acid ethyl ester in 50 ml of toluene is added dropwise with stirring. Thereafter, the mixture is stirred for a further two hours. After filtration, the filtrate is washed free of halide with water and evaporated to dryness. A yellowish oil, which is recrystallized from diisopropanol ether, is obtained as the residue. 22.7 g (94 percent of theory) of 1-diphenylmethyl-3-methyl-3-(3,4-dimethoxybenzyl)-4-carbethoxy-piperazine are obtained. m.p. = 113° C.

In an analogous fashion the following compounds are obtained. (D)-1-diphenylmethyl-3-methyl-3-(3,4-dimethoxybenzyl)-4-carbethoxypiperazine m.p. = 101° C. (diisopropylether); $[\alpha]_D^{20} = +10°$ (c = 1, methanol); (L)-1-diphenylmethyl-3-methyl-3-(3,4-dimethoxybenzyl)-4-carbethoxypiperazine m.p. = 102° C. (diisopropylether); $[\alpha]_D^{20} = -10.4°$ (c = 1, methanol); (D)-1-(p-chlorophenyl-phenylmethyl)-3-methyl-3-(3,4-dimethoxybenzyl)-4-carbethoxy-piperazine-hydrochloride m.p. = 156° C. (isopropanol); $[\alpha]_D^{20} = +12.0°$ (c = 1, methanol); and (L)-1-(p-chlorophenyl-phenylmethyl)-3-methyl-3-(3,4-dimethoxyphenyl)-carbethoxy-piperazine-hydrochloride m.p. = 157° C. (isopropanol); $[\alpha]_D^{20} = -12.2°$ (c = 1, methanol).

EXAMPLE 6

21.5 g of 1-diphenylmethyl-3-methyl-3-(3,4-dimethoxybenzyl)-piperazine (cf. Example 2) are dissolved in 200 ml of dry toluene, 5.2 g of triethylamine are added, and the mixture is combined with stirring with a solution of 4.1 g of acetyl chloride in 50 ml of dry toluene. Thereupon, the mixture is stirred for a further eight hours. The mixture is filtered and the filtrate washed halide-free with water and concentrated. An oil remains, which is recrystallized from diisopropylether.

20.7 g (90.5 percent of theory) of 1-diphenylmethyl-3-methyl-3-(3,4-dimethoxybenzyl)-4-acetyl-piperazine are obtained. m.p. = 116° C.

In an analogous fashion, in the same yield, the following are obtained: (D)-1-diphenylmethyl-3-methyl-3-(3,4-dimethoxybenzyl)-4-acetyl-piperazine m.p. = 152° C. (isopropanol); $[\alpha]_D^{20} = +8.4°$ (c = 1, methanol); and (L)-1-diphenylmethyl-3-methyl-3-(3,4-dimethoxybenzyl)-4-acetyl-piperazine m.p. = 153° C. (isopropanol); $[\alpha]_D^{20} = -8.5°$ (c = 1, methanol).

EXAMPLE 7

50 g of 1-diphenylmethyl-3-methyl-3-(3,4-dimethoxybenzyl)-piperazine (cf. Example 2) are dissolved in 200 ml of benzene and 400 ml of methanol and heated for 48 hours in a pressure vessel at 60° C. with addition of 22 g of ethylene oxide. Subsequently, the solution is evaporated to dryness. The residue is dissolved in 500 ml of diethylether, combined with 60 ml of 2N HCl, and vigorously stirred. The organic phase is separated and washed halide-free with water. The aqueous acid extract is alkalized with ammonium hydroxide solution and extracted with diethyl ether. The extract is dried, filtered, and the solvent is removed by distillation. 54 g (98 percent of theory) of 1-diphenylmethyl-3-methyl-3-(3,4-dimethoxybenzyl)-4-hydroxyethylpiperazine are obtained as a colorless resin.

On stirring with water, a solid product is obtained which can be air-dried and contains 1 mol of water.

| Analysis: | C | H | N |
|---|---|---|---|
| Calculated | 71.3 | 8.0 | 5.9 |
| Found | 71.3 | 8.2 | 6.2 |

In an analogous fashion are obtained: (D)-1-diphenylmethyl-3-methyl-3-(3,4-dimethoxybenzyl)-4-hydroxyethyl-piperazine. This is a solid without a definite melting point, yield 87 percent. $[\alpha]_D^{20} = +9.0°$ (c = 1, methanol); (dihydrochloride) m.p. = 208° C. (ethanol); $[\alpha]_D^{20} = -5.8°$ (c = 6.7, methanol); and (L)-1-diphenylmethyl-3-methyl-3-(3,4-dimethoxybenzyl)-4-hydroxyethyl-piperazine. This is a solid product without definite melting point, yield 85 percent $[\alpha]_D^{20} = -9.1°$ (c = 1, methanol); (dihydrochloride) m.p. = 209° C. (ethanol); $[\alpha]_D^{20} = +5.6°$ (c = 6.7, methanol); 1-(p-chlorophenyl-phenylmethyl)-3-methyl-3-(3,4-dimethoxybenzyl)-4-hydroxyethyl-piperazine m.p. = 121° C. (methanol); (D)-1-(p-chlorophenyl-phenylmethyl)-3-methyl-3-(3,4-dimethoxybenzyl)-4-hydroxyethyl-piperazine. This is a solid product without definite melting point. $[\alpha]_D^{20} = -14.8°$ (c = 1, methanol); and (L)-1-(p-chlorophenyl-phenylmethyl)-3-methyl-3-(3,4-dimethoxybenzyl)-4-hydroxyethyl-piperazine. This is obtained as a solid product without definite melting point. $[\alpha]_D^{20} = +14.1°$ (c = 1, methanol).

EXAMPLE 8

4.3 g of 1-diphenylmethyl-3-methyl-3-(3,4-dimethoxybenzyl)-4-hydroxyethyl-piperazine (cf. Example 7) are added dropwise with stirring to a suspension of 0.44 g of sodium hydride in mineral oil in 20 ml of dry dimethylformamide and the mixture is heated to 80° C. After 1 hour, a solution of 2.1 g of 3,4,5-trimethoxybenzoylchloride in 10 ml of dry dimethylformamide is added dropwise and the suspension is stirred at room temperature for two days. After distillative removal of the solvent, the residue is dissolved in 100 ml of toluene, washed free of halide with a little water, and concentrated. The oily residue is dissolved in 100 ml of diethylether. The dihydrochloride is formed with hydrogen chloride, filtered, and recrystallized from isopropanol. 5 g (74.4 percent of theory) of 1-diphenylmethyl-3-methyl-3-(3,4-dimethoxybenzyl)-4-β-(3,4,5-trimethoxybenzoyl-oxyethyl)-piperazine-dihydrochloride are obtained. m.p. = 202° C.

In a similar fashion, there are obtained: 1-diphenylmethyl-3-methyl-3-(3,4-dimethoxybenzyl)-4-β-(pyridine-3-carbonyl-oxyethyl)-piperazine-trihydrochloride m.p. = 210° C. (methanol); and 1-(p-chlorophenyl-phenylmethyl)-3-methyl-3-(3,4-dimethoxybenzyl)-4-β-(pyridine-3-carbonyl-oxyethyl)-piperazine-trihydrochloride m.p. = 188° C. (ethanol).

1-(p-chlorophenyl-phenylmethyl)-3-methyl-3-(3,4-dimethoxybenzyl)-4-β-(3,4,5-trimethoxybenzoyl-oxyethyl)-piperazine is obtained in an analogous fashion as a glass-like solid resin without definite melting point.

| Analysis: | C | H | N | Cl |
|---|---|---|---|---|
| Calculated | 68.0 | 6.6 | 4.1 | 5.1 |
| Found | 67.8 | 6.6 | 4.1 | 5.0 |

EXAMPLE 9

If (D)-1-diphenylmethyl-3-methyl-3-(3,4-dimethoxybenzyl)-piperazine is reacted with propylene oxide under the same conditions described in Example 7, then (D)-1-diphenylmethyl-3-methyl-3-(3,4-dimethoxybenzyl)-4-(2-hydroxypropyl)-piperazine-dihydrochloride is obtained. m.p. = 217° – 219° C. (ethanol); $[\alpha]_{365\ nm}^{20} = -9.1°$ (c = 1, methanol).

In an analogous fashion are obtained: (L)-1-diphenylmethyl-3-methyl-3-(3,4-dimethoxybenzyl)-4-(2-hydroxypropyl)-piperazine-dihydrochloride m.p. = 218° – 220° C. (ethanol); $[\alpha]_{365\ nm}^{20} = +9.3°$ (c = 1, methanol); (D)-1-(p-chlorophenyl-phenylmethyl)-3-methyl-3-(3,4-dimethoxybenzyl)-4-propanol-(2)-piperazine-dihydrochloride m.p. = 219° – 222° C. (ethanol); $[\alpha]_{365\ nm}^{20} = -4.2°$ (c = 1, methanol); and (L)-1-(p-chlorophenyl-phenylmethyl)-3-methyl-3-(3,4-dimethoxybenzyl)-4-propanol-(2)-piperazine-dihydrochloride m.p. = 220° – 222° C. (ethanol); $[\alpha]_D^{20} = +4.4°$ (c = 1, methanol).

EXAMPLE 10

A solution of 55.6 g of 3-methyl-3-(3,4-dimethoxybenzyl)-4-methyl-piperazinone-(2) (cf. "Preparation", part 2 above) in 300 ml of dry tetrahydrofuran is added dropwise over a period of two hours to a suspension of 11.6 g of lithium aluminum hydride in 1600 ml of dry tetrahydrofuran, with stirring and at the boiling point. The reaction solution is heated at the boiling point for a further two hours with stirring. After the careful addition of water, insolubles are separated by filtration and the filtrate is evaporated and distilled to dryness. At 163° – 165° C. (5 × 10⁻² mm Hg), 48.5 g (92 percent of theory) of 3-methyl-3-(3,4-dimethoxybenzyl)-4-methylpiperazine distill over.

In a similar fashion and in a similar yield, the following compounds are prepared: (D)-3-methyl-3-(3,4-dimethoxybenzyl)-4-methyl-piperazine b.p. = 164° – 166° C. (0.7 mm Hg); $[\alpha]_D^{20} = -22.9°$ (c = 1, methanol); and (L)-3-methyl-3-(3,4-dimethoxybenzyl)-4-methyl-piperazine b.p. = 164° – 166° C. (0.5 mm Hg); $[\alpha]_D^{20} = +22.7°$ (c = 1, methanol).

EXAMPLE 11

13.3 g of 3-methyl-3-(3,4-dimethoxybenzyl)-4-methylpiperazine (cf. Example 10) are brought to boiling with 13.8 g of dry potassium carbonate and 0.1 g of potassium iodide in 75 ml of dry acetone and are combined under reflux and with stirring with 12.3 g of diphenylmethyl bromide in 25 ml of dry acetone. After five hours, the mixture is cooled and filtered. The filtrate is evaporated to dryness. The oily residue is taken up in 150 ml of toluene and washed free of halide with water. The organic phase is evaporated and the oily residue is dissolved in 120 ml of diethyl ether. After the introduction of hydrogen chloride, the dihydrochloride formed is removed by filtration, washed with diethyl ether, and recrystallized from a little ethyl alcohol. 13.7 g (85 percent of theory) of 1-diphenylmethyl-3-methyl-3-(3,4-dimethoxybenzyl)-4-methyl-piperazine-dihydrochloride are obtained. m.p. = 193° C.

Correspondingly, the following compounds are obtained in similar yields:

(D)-1-diphenylmethyl-3-methyl-3-(3,4-dimethoxybenzyl)-4-methyl-piperazine. m.p. = 102° C. (diisopropylether); $[\alpha]_D^{20} = -20.4°$ (c = 1, methanol); and (L)-1-diphenylmethyl-3-methyl-3-(3,4-dimethoxybenzyl)-4-methyl-piperazine. m.p. = 102° C. (diisopropylether); $[\alpha]_D^{20} = +20.2°$ (c = 1, methanol).

The compounds in Example 4a, $a_1$ - $j$, $j_1$, $l_1$, and $l_2$ were prepared in an analogous fashion.

EXAMPLE 12

8.6 g of 1-diphenylmethyl-3-methyl-3-(3,4-dimethoxybenzyl)-piperazinone-(2) [cf. "Preparation", part 3(C) above] are dissolved in 80 ml of absolute tetrahydrofuran and added dropwise over 2 hours, at the boiling point, to a stirred suspension of 2.3 g of lithium aluminum hydride in 80 ml of tetrahydrofuran. The suspension is heated for a further six hours with reflux and stirring. After the careful addition of water and filtration, the solvent is distilled off. An oil is obtained, which is recrystallized from diethylether. 7.7 g (92.5 percent of theory) of 1-diphenylmethyl-3-methyl-3-(3,4-dimethoxybenzyl-piperazine are obtained. m.p. = 123° C.

In a similar fashion and in a similar yield, the following substances were prepared: (D)-1-diphenylmethyl-3-methyl-3-(3,4-dimethoxybenzyl)-piperazine m.p. = 136° C. (diisopropylether); $[\alpha]_D^{20} = +19.5°$ (c = 1, methanol); and (L)-1-diphenylmethyl-3-methyl-3-(3,4-dimethoxybenzyl)-piperazine m.p. = 137° C. (diisopropylether); $[\alpha]_D^{20} = -19.8°$ (c = 1, methanol).

By the same method, the 1-(p-chlorophenyl-phenyl-methyl)-3-methyl-3-(3,4-dimethoxybenzyl)-piperazine described in Example 3 is obtained in the form of the racemate as well as the optical antipodes.

EXAMPLE 13

22.2 g of 1-diphenylmethyl-3-methyl-3-(3,4-dimethoxybenzyl)-4-methyl-piperazinone-(2) (cf. "Preparation", 4) are dissolved in 200 ml of dry tetrahydrofuran and added dropwise over a period of 2 hours, with stirring, to a boiling suspension of 5.75 g of lithium aluminum hydride in 400 ml of dry tetrahydrofuran. The mixture is heated to boiling for a further 3 hours. After careful addition of water, the mixture is filtered and the filtrate evaporated. The remaining oil is further worked up as in Example 4. 20 g (80 percent of theory) of 1-diphenylmethyl-3-methyl-3-(3,4-dimethoxybenzyl)-4-methyl-piperazine are obtained in the form of the dihydrochloride. m.p. = 192° C. (ethanol).

All compounds mentioned in Example 4 through 4j, $j_1$, and $l$ through $l_2$ are obtained in an analogous fashion.

Obtained in a similar fashion are: (D)-1-diphenylmethyl-3-(3,4-diethoxybenzyl)-4-methylpiperazine. m.p. = 105° – 107° C. (diisopropylether); $[\alpha]_D^{20} = -22.3°$ (c = 1, methanol); and (L)-1-diphenylmethyl-3-(3,4-diethoxyphenyl)-4-methyl-piperazine m.p. = 107° C. (diisopropylether); $[\alpha]_D^{20} = +15.5°$ (c = 1, methanol).

EXAMPLE 14

9.16 g of (D)-1-diphenylmethyl-3-methyl-3-(3,4-dimethoxybenzyl)-4-acetyl-piperazine (cf. Example 6) are dissolved in 150 ml of dry tetrahydrofuran and the solution is added dropwise, with stirring and over a period of two hours, to a boiling suspension of 2.3 g of lithium aluminum hydride in 150 ml of dry tetrahydrofuran. The mixture is held at the boil for a further three hours. After the careful addition of water, the batch is filtered and the filtrate is evaporated. The remaining oil is crystallized out of a little isopropanol. 7.2 g (81 percent of theory) of (D)-1-diphenylmethyl-3-methyl-3-(3,4-dimethoxybenzyl)-4-ethyl-piperazine are obtained. m.p. = 122° C.; $[\alpha]_D^{20} = -16.1°$ (c = 1, methanol).

In an analogous fashion, the compounds named in Example 4 $a_1$, $b$ – $c_1$, and $i$ – $j_1$ are obtained.

EXAMPLE 15

14.5 g of 1-diphenylmethyl-3-methyl-3-(3,4-dimethoxybenzyl)-4-carbethoxy-piperazine (cf. Example 5) are dissolved in 170 ml of dry tetrahydrofuran and added dropwise, with stirring over a period of two hours, to a boiling suspension of 3.42 g of lithium aluminum hydride in 150 ml of dry tetrahydrofuran. The batch is kept at the boiling point for a further 2 hours. After careful addition of water, the mixture is filtered and the filtrate evaporated. The remaining oil is further worked up as in Example 4. 12.4 g (82 percent of theory) of 1-diphenylmethyl-3-methyl-3-(3,4-dimethoxybenzyl)-4-methyl-piperazine are obtained in the form of the dihydrochloride. m.p. = 192° C. (ethanol).

In an analogous fashion, the two optical antipodes mentioned in Example 4 are obtained, as well as the compounds mentioned in Example 4 1 – $l_2$.

EXAMPLE 16

Tablets of the following composition were prepared in a tablet press in the conventional fashion:
200.00 mg of (D)-1-diphenylmethyl-3-methyl-3-(3,4-dimethoxybenzyl)-4-methyl-piperazine;
150.00 mg corn starch;
13.50 mg of gelatin;
45.00 mg of lactose;

22.50 mg of talc;
2.25 mg of chemically pure submicroscopically divided silicic acid ("Aerosil"); and
6.75 mg of potato starch (as a 6 percent paste).

EXAMPLE 17

Dragées of the following composition were prepared in the usual fashion:
100.00 mg of (D)-1-diphenylmethyl-3-methyl-3-(3,4-dimethoxybenzyl)-4-methyl-piperazine;
170.00 mg of core mass; and
160.00 mg of sugaring mass.

The core mass comprises 9 parts of corn starch, 3 parts of lactose, and 1 part of a 60:40 vinyl pyrrolidone:vinyl acetate copolymer ("Luviskol VA 64", cf. Pharm. Ind. 1962, 586).

The sugaring mass comprises 5 parts of cane sugar, 2 parts of corn starch, 2 parts of calcium carbonate, and 1 part of talc. The dragées prepared in this manner are subsequently provided with a coating resistant to stomach juices.

EXAMPLE 18

50 g of (D)-1-diphenylmethyl-3-methyl-3-(3,4-dimethoxybenzyl)-4-methyl-piperazine lactate are dissolved in 5 liters of water, adjusted isotonically with sodium chloride, and used to fill sterile ampules holding 5 ml.

What is claimed is:
1. A piperazine compound of the formula

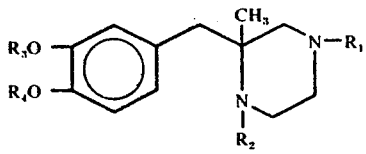

and salts thereof with a physiologically tolerable acid, wherein $R_1$ is diphenylmethyl, in the phenyl groups of which the para-hydrogen may be replaced by chlorine; $R_2$ is hydrogen, straight chain alkyl having 1 – 5 carbon atoms, alkenyl having 3 to 4 carbon atoms, or hydroxyalkyl having 2 – 4 carbon atoms; and $R_3$ and $R_4$, which are the same or different, are alkyl having 1 – 4 carbon atoms.

2. A compound as in claim 1 which is 1-diphenylmethyl-3-methyl-3-(3,4-dimethoxybenzyl)-piperazine.

3. A compound as in claim 1 which is (D)-1-diphenylmethyl-3-methyl-3-(3,4-dimethoxybenzyl)-piperazine.

4. A compound as in claim 1 which is (L)-1-diphenylmethyl-3-methyl-3-(3,4-dimethoxybenzyl)-piperazine.

5. A compound as in claim 1 which is 1-(p-chlorophenylphenylmethyl)-3-methyl-3-(3,4-dimethoxybenzyl)-piperazine.

6. A compound as in claim 1 which is (D)-1-(p-chlorophenylphenylmethyl)-3-methyl-3-(3,4-dimethoxybenzyl)-piperazine.

7. A compound as in claim 1 which is (L)-1-(p-chlorophenyl-phenylmethyl)-3-methyl-3-(3,4-dimethoxybenzyl)-piperazine.

8. A compound as in claim 1 which is 1-diphenylmethyl-3-methyl-3-(3,4-dimethoxybenzyl)-4-methyl-piperazine.

9. A compound as in claim 1 which is (D)-1-diphenylmethyl-3-methyl-3-(3,4-dimethoxybenzyl)-4-methyl-piperazine.

10. A compound as in claim 1 which is (L)-1-diphenylmethyl-3-methyl-3-(3,4-dimethoxybenzyl)-4-methyl-piperazine.

11. A compound as in claim 1 which is (D)-1-diphenylmethyl-3-methyl-3-(3,4-dimethoxybenzyl)-4-ethyl-piperazine.

12. A compound as in claim 1 which is (L)-1-diphenylmethyl-3-methyl-3-(3,4-dimethoxybenzyl)-4-ethyl-piperazine.

13. A compound as in claim 1 which is (D)-1-diphenylmethyl-3-methyl-3-(3,4-dimethoxybenzyl)-4-n-propyl-piperazine.

14. A compound as in claim 1 which is (L)-1-diphenylmethyl-3-methyl-3-(3,4-dimethoxybenzyl)-4-n-propyl-piperazine.

15. A compound as in claim 1 which is (D)-1-diphenylmethyl-3-methyl-3-(3,4-dimethoxybenzyl)-4-n-butyl-piperazine.

16. A compound as in claim 1 which is (L)-1-diphenylmethyl-3-methyl-3-(3,4-dimethoxybenzyl)-4-n-butyl-piperazine.

17. (D)-1-diphenylmethyl-3-methyl-3-(3,4-dimethoxybenzyl)-4-n-hexyl-piperazine.

18. (L)-1-diphenylmethyl-3-methyl-3-(3,4-dimethoxybenzyl)-4-n-hexyl-piperazine.

19. (D)-1-diphenylmethyl-3-methyl-3-(3,4-dimethoxybenzyl)-4-n-heptyl-piperazine.

20. (L)-1-diphenylmethyl-3-methyl-3-(3,4-dimethoxybenzyl)-4-n-heptyl-piperazine.

21. (D)-1-diphenylmethyl-3-methyl-3-(3,4-dimethoxybenzyl)-4-n-octylpiperazine.

22. (L)-1-diphenylmethyl-3-methyl-3-(3,4-dimethoxybenzyl)-4-n-octyl-piperazine.

23. A compound as in claim 1 which is (D)-1-diphenylmethyl-3-methyl-3-(3,4-dimethoxybenzyl)-4-allyl piperazine-dihydrochloride.

24. A compound as in claim 1 which is (L)-1-diphenylmethyl-3-methyl-3-(3,4-dimethoxybenzyl)-4-allyl-piperazine-dihydrochloride.

25. A compound as in claim 1 which is (D)-1-diphenylmethyl-3-methyl-3-(3,4-dimethoxybenzyl)-4-(1-yl-2-butene)-piperazine-dihydrochloride.

26. A compound as in claim 1 which is (L)-1-diphenylmethyl-3-methyl-3-(3,4-dimethoxybenzyl)-4-(1-yl-2-butene)-piperazinedihydrochloride.

27. A compound as in claim 1 which is 1-(p-chlorophenylphenylmethyl)-3-methyl-3-(3,4-dimethylbenzyl)-4-methyl-piperazinedihydrochloride.

28. A compound as in claim 1 which is (D)-1-(p-chlorophenyl-phenylmethyl)-3-methyl-3-(3,4-dimethoxybenzyl)-4-methyl-piperazine-dihydrochloride.

29. A compound as in claim 1 which is (L)-1-(p-chlorophenyl-phenylmethyl)-3-methyl-3-(3,4-dimethoxybenzyl)-4-methyl-piperazine-dihydrochloride.

30. A compound as in claim 1 which is 1-diphenylmethyl-3-methyl-3-(3,4-dimethoxybenzyl)-4-hydroxyethyl-piperazine.

31. A compound as in claim 1 which is (D)-1-diphenylmethyl-3-methyl-3-(3,4-dimethoxybenzyl)-4-hydroxyethyl-piperazine.

32. A compound as in claim 1 which is (L)-1-diphenylmethyl-3-methyl-3-(3,4-dimethoxybenzyl)-4-hydroxyethyl-piperazine.

33. A compound as in claim 1 which is 1-(p-chlorophenylphenylmethyl)-3-methyl-3-(3,4-dimethoxybenzyl)-4-hydroxyethyl-piperazine.

34. A compound as in claim 1 which is (D)-1-(p-chlorophenyl-phenylmethyl)-3-methyl-3-(3,4-dimethoxybenzyl)-4-hydroxyethyl-piperazine.

35. A compound as in claim 1 which is (L)-1-(p-chlorophenyl-phenylmethyl)-3-methyl-3-(3,4-dimethoxybenzyl)-4-hydroxyethyl-piperazine.

36. A compound as in claim 1 which is (D)-1-diphenylmethyl-3-methyl-3-(3,4-dimethoxybenzyl)-4-(2-hydroxypropyl)-piperazine.

37. A compound as in claim 1 which is (L)-1-diphenylmethyl-3-methyl-3-(3,4-dimethoxybenzyl)-4-(2-hydroxypropyl)-piperazine.

38. A compound as in claim 1 which is (D)-1-(p-chlorophenyl-phenylmethyl)-3-methyl-3-(3,4-dimethoxybenzyl)-4-propanol-(2)-piperazine.

39. A compound as in claim 1 which is (L)-1-(p-chlorophenylphenylmethyl)-3-methyl-3-(3,4-dimethoxybenzyl)-4-propanol-(2)-piperazine.

40. A compound as in Claim 1 which is (D)-1-diphenylmethyl-3-(3,4-diethoxybenzyl)-4-methyl-piperazine-dihydrochloride.

41. A compound as in Claim 1 which is (L)-1-diphenylmethyl-3-(3,4-diethoxybenzyl)-4-methyl-piperazine-dihydrochloride.

42. A therapeutic composition consisting essentially of a pharmaceutical excipient and an effective amount of a piperazine compound as in claim 1, or of a salt thereof with a therapeutically tolerable acid, as the active ingredient.

43. The method of treating cardiac disease in a patient suffering therefrom which comprises administering an effective amount of a piperazine compound as in claim 1, or a salt thereof with a physiologically tolerable acid.

* * * * *